United States Patent [19]
Poehner et al.

[11] Patent Number: 4,926,457
[45] Date of Patent: May 15, 1990

[54] RADIOLUCENT HOSPITAL BED SURFACE

[75] Inventors: Michael E. Poehner, West Harrison, Ind.; Michael J. Duwell, Cincinnati, Ohio; Howard J. Boyd, Oldenburg, Ind.

[73] Assignee: Hill-Rom Company, Inc., Batesville, Ind.

[21] Appl. No.: 150,075

[22] Filed: Jan. 29, 1988

[51] Int. Cl.$^5$ .............................................. A61B 6/04
[52] U.S. Cl. ..................................... 378/209; 378/208
[58] Field of Search ................. 378/208, 209; 128/70; 5/66; 269/322–324, 328

[56] References Cited

U.S. PATENT DOCUMENTS

| | | |
|---|---|---|
| 3,783,863 | 1/1974 | Kliever ................. 378/209 |
| 3,897,345 | 7/1975 | Foster . |
| 3,947,686 | 3/1976 | Cooper et al. . |
| 4,134,019 | 1/1979 | Koontz et al. . |
| 4,145,612 | 3/1979 | Cooper . |
| 4,146,793 | 3/1979 | Bergstrom et al. . |
| 4,148,472 | 3/1979 | Rais et al. ............ 378/209 |
| 4,197,464 | 4/1980 | Amor . |
| 4,252,594 | 2/1981 | Cooper . |
| 4,262,204 | 4/1981 | Mirabella . |
| 4,501,414 | 2/1985 | Mason et al. ......... 378/209 |

FOREIGN PATENT DOCUMENTS 3405425 8/1985 Fed. Rep. of Germany ...... 378/209

Primary Examiner—Carolyn E. Fields
Assistant Examiner—David P. Porta
Attorney, Agent, or Firm—Wood, Herron & Evans

[57] ABSTRACT

Multiple elements of a blow-molded, integral patient support surface each include a synthetic sheet-like patient support element and an underlying synthetic corrugated reinforcing element spaced from the support element. When loaded, the patient support element engages the corrugated reinforcing element which resists deflection and rigidifies the surface. The corrugation angulation and the combined wall thicknesses of the flat support and corrugated reinforcing elements in a predetermined are are selected to provide an effective combined wall thickness within F.D.A. attenuation standards, yet still provide sufficient rigidity and aberration-free x-rays.

An adjustable x-ray plate cassette is disclosed.

36 Claims, 4 Drawing Sheets

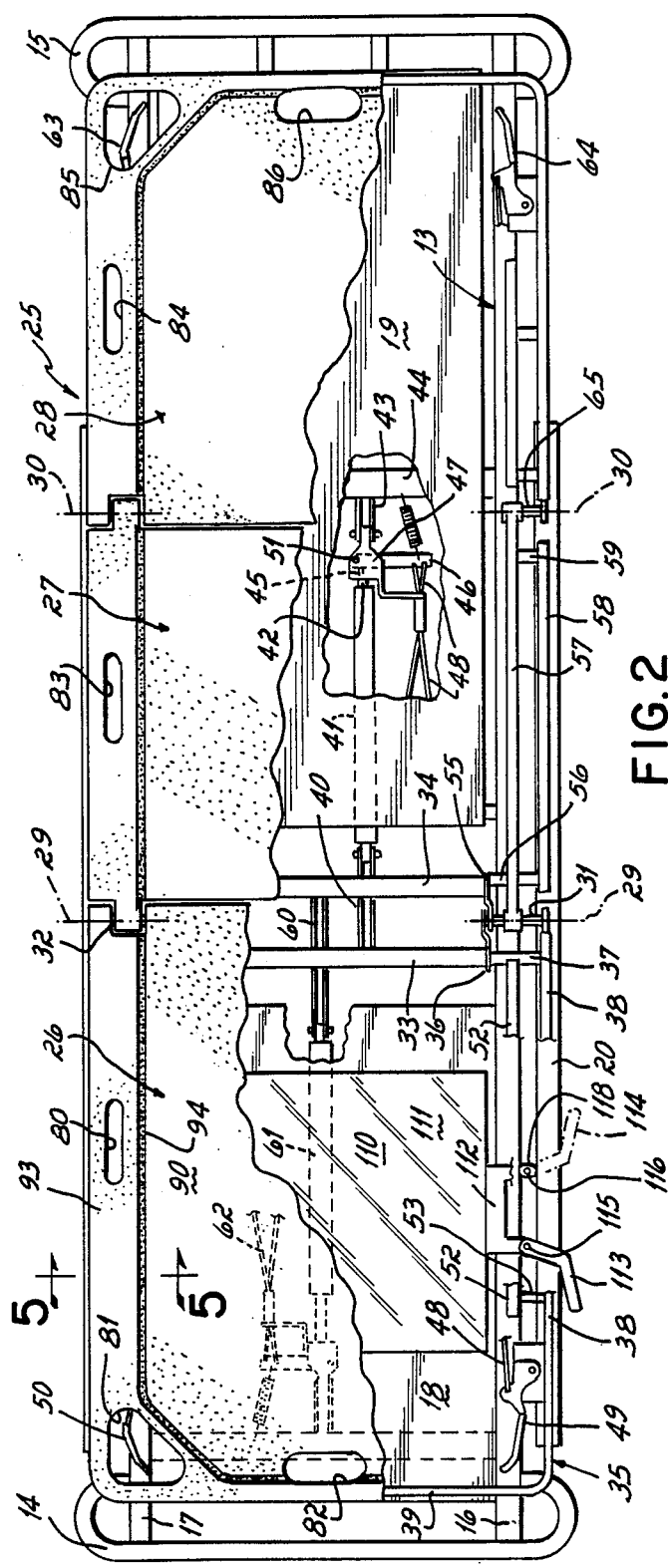
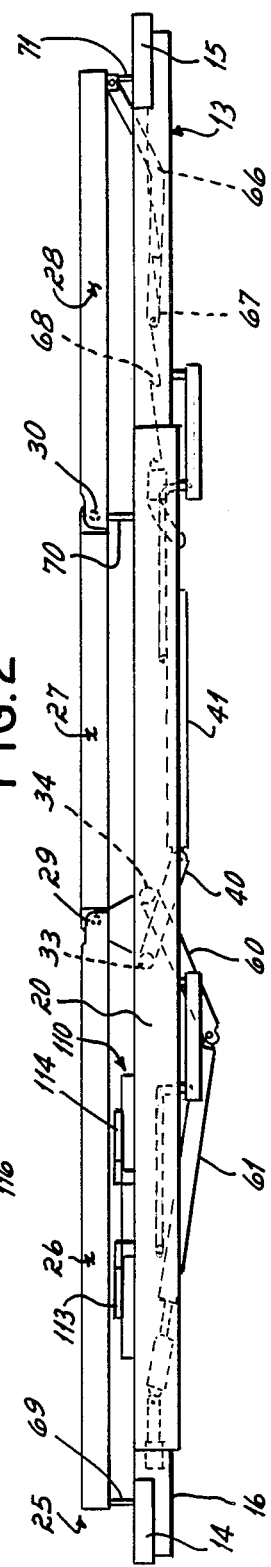
FIG.2
FIG.3

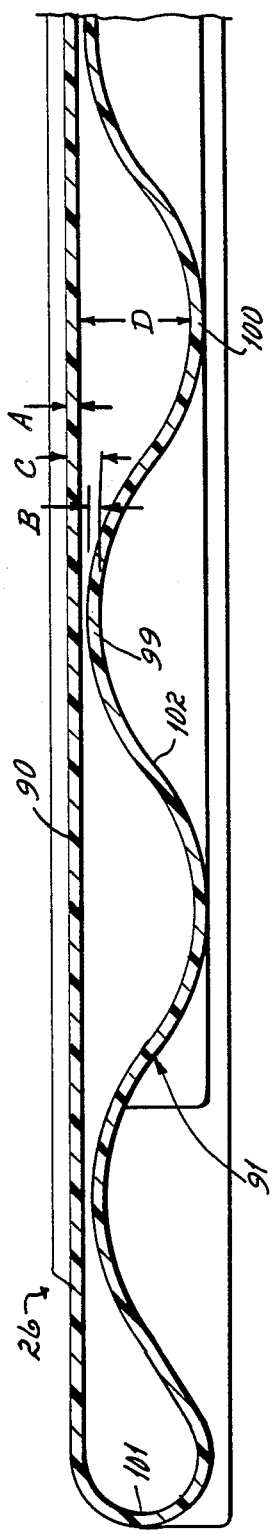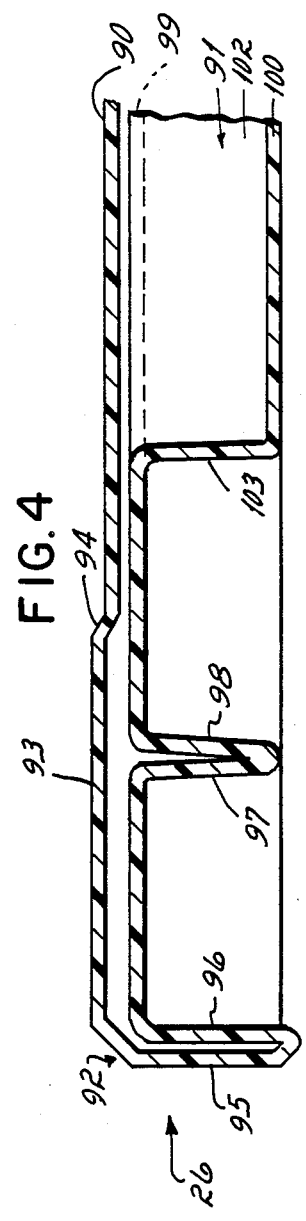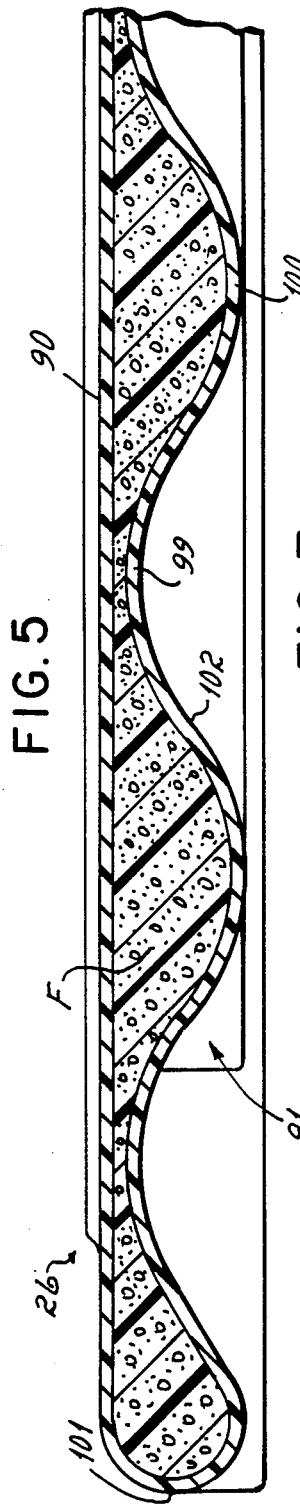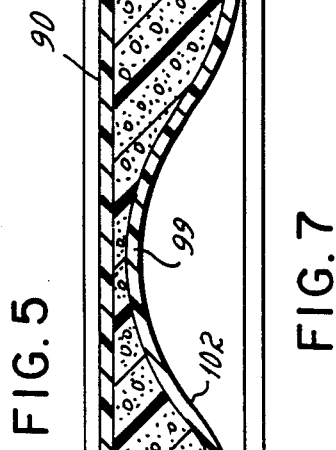

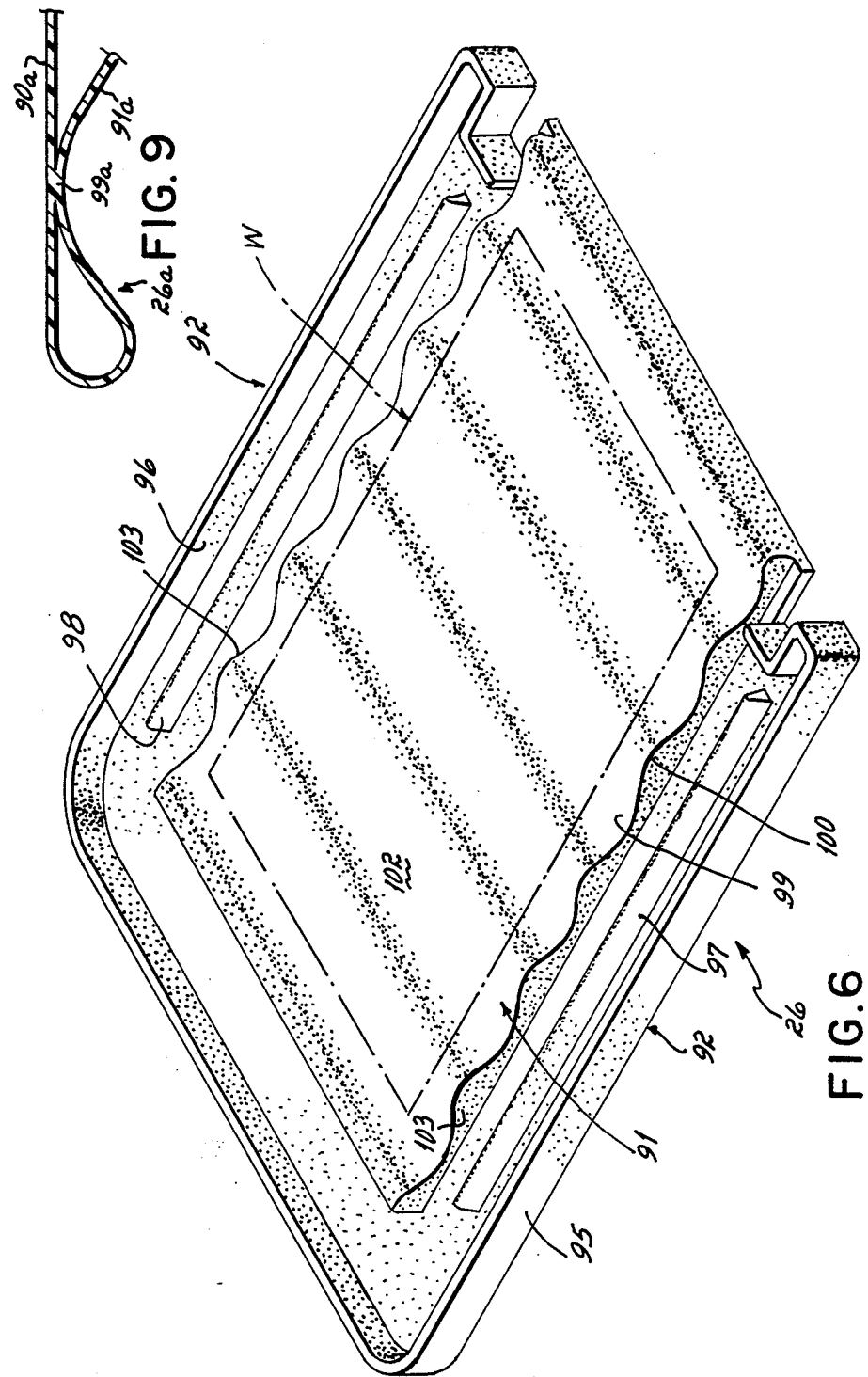

RADIOLUCENT HOSPITAL BED SURFACE

This invention relates to patient supports and more particularly to radiolucent patient support surfaces.

The varied environments in which radiolucent patient supports are required are attended by certain characteristics which make even present day supports insufficient for universal use. Many such current supports are highly specialized for particular applications, such as the cantilevered, extendible supports used in large, immobile tomography apparatus, or the rigid support tables provided on x-ray machines. While useful for their intended special function with the noted equipment, these supports are not generally useful in hospital patient support applications where many other parameters must be considered.

For example, and particularly with respect to patient supports or stretchers used in emergency, critical care, or out-patient areas, mobility of the entire support structure and articulation of support surfaces are important features. Stiffness of the surface is also of prime importance, due to stresses placed on the surfaces during certain procedures. The vigorous chest compression forces generated in the performance of CPR, for example, tend to deflect the patient support. It must be of rigid construction in order to withstand repeated use without fatigue and failure.

At the same time, it is desirable to use x-ray, fluoroscopy, or "C"-arm mounted diagnostic or treatment equipment with a patient supported on a surface support of the type used in emergency, critical care, or out-patient areas. For this reason, the support must comply with the one millimeter of Series 1100 aluminum equivalency attenuation standard of the United States Food and Drug Administration (F.D.A.). This standard requires that any surface or structure lying in the wave path must produce no more attenuation than a Series 1100 aluminum sheet one millimeter thick. This attenuation standard makes it difficult to increase support rigidity without additional structure which would further attenuate wave energy.

The stretcher manufacturer is thus caught between the necessity of providing an articulated but rigid patient support structure capable of withstanding repeated stresses such as those produced in CPR procedures on the one hand and the limitation of the F.D.A.'s one millimeter aluminum equivalency standard on the other hand. When the support is strengthened by additional structure or increased support thicknesses to increase rigidity, the equivalency standard is breached, or the reinforcing structure within the x-ray area causes aberrations on the x-ray film plate.

In an effort to provide a stress-resisting patient support, and to meet the F.D.A. radiolucency standard, hospital beds or stretchers have historically been constructed of aluminum or steel sheet, with an aluminum patient support pan, for example, riveted to a support frame.

More recently, a variety of sheet plastics have been utilized for the pans to allow for radiolucency of the surface. This increasing use of plastics is driven by an increased frequency of use of portable x-ray and C-arm apparatus in the patient and emergency room areas. While plastics thicker than one millimeter may meet the F.D.A. equivalency standard, their relatively poor structural characteristics require wall thicknesses of ⅜" to ½" to provide some degree of rigidity. Tolerances become very critical as the thicknesses required for rigidity approach the one millimeter of aluminum equivalency standard.

Such aluminum or plastic surfaces as are currently in use do not generally perform well in excessive loading situations, and may flex too much in CPR activities, for example, where downward forces applied to a patient's torso stress the bed surface. The patient surface deflects and "oil cans", bows or creases. Such flexing can elongate the pan-to-frame rivet holes. Eventually, a new replacement pan is required. Flexing at notches on plastic material surfaces causes them to fatigue and fail. Moreover, joints associated with the prior pans and frames are difficult to clean of blood or other fluids.

It is thus desirable to provide an improved patient support surface which is both sufficiently rigid and strong enough to withstand repeated stress, such as produced in CPR procedures without undue fatigue and failure, and at the same time is sufficiently radiolucent in a predetermined area to meet or exceed the F.D.A. one millimeter of aluminum equivalency attenuation standard and to provide a clear x-ray plate without aberrations or artifacts due to support surface structure.

Accordingly, it has been one objective of this invention to provide an improved radiolucent patient support.

A further objective has been to provide an improved radiolucent articulated hospital bed or stretcher surface.

A further objective of this invention has been to provide a reinforced radiolucent hospital bed or stretcher surface providing reduced, uniform, electromagnetic wave attenuation.

A further objective of the invention has been to provide an improved radiolucent hospital bed or stretcher surface having uniform electromagnetic wave attenuation and being capable of withstanding CPR stresses without undesirable flex and surface fatigue.

A still further objective of the invention has been to provide an improved rigid patient surface constructed from thin plastic material and providing an x-ray window within applicable F.D.A. standards without producing aberrations or diagnostically significant artifact. In another aspect of the invention, it has also been an objective to provide an improved x-ray plate cassette.

To these ends, a preferred embodiment of the invention is based on applicant's discovery that a white or light-colored plastic patient support sheet typically about 0.093" in thickness for a preferred material, backed up by a slightly spaced apart corrugated sheet of the same thickness where the corrugated walls do not exceed an included angle of about 45° with respect to the support surface, will uniformly attenuate electromagnetic wave energy within the F.D.A. equivalency standard, without producing aberration or diagnostically significant artifact, and at the same time will provide sufficient resistance to deflection so as to withstand procedural stresses such as those generated in the delivery of CPR. The preferred embodiment comprises a hospital bed or stretcher surface having a flat sheet-like patient support element, and an underlying ribbed, sheet-like reinforcing element. Both sheets are made of synthetic materials and their combined wall thickness, over a predetermined area, is substantially uniform. The ribbed reinforcing element is a corrugated sheet having a plurality of transversely directed and parallel ribs or corrugations. The crests of the ribs are normally spaced from the patient support element, but engage and support that element when that element is slightly deflected. The curving walls of the corrugated reinforcing element are maintained at angles of less than 45° with respect to the plane of the patient support element such that the effective wall thickness of the two overlying elements throughout a predetermined area of the surface is uniform, and substantially equal to the combined thicknesses of the sheet material in each element. Preferably, the patient support and reinforcing elements are blow-molded in an integral piece. Joints and overlaps of material are eliminated. This makes the support more rigid and easier to clean.

By careful choice of the molecular weight of the polymer chosen and the type of manufacturing process, it is possible for the crests of the ribs to be "kissed off" or touch the patient support element. In the preferred embodiment herein described, this contact is avoided. However, use of a lower molecular weight material and a more dimensionally accurate process, for example injection molding, could allow this contact of the sections to take place. Such contact may include an integral contact of rib crests with the patient surface element wherein the material is fused together.

There are no vertical walls in the surface within the predetermined x-ray window to cause nonuniform wave attenuation. The F.D.A. one millimeter of aluminum equivalency standard is met, yet the patient support element is adequately supported by the reinforcing element against fatiguing flex. CPR related and other stresses, can thus be applied to the surface without undue deformation, while accurate x-ray and other wave diagnostic or treatment processes can be provided without aberration due to the surface structure and without excessive dosing.

An improved x-ray plate holding cassette is also provided with handles operatively coupled to cams for adjustably securing the cassette underneath the patient support by interacting with adjacent frames or rails of the support.

These and other objects and advantages will become even more readily apparent from the following description of a preferred embodiment of the invention, and from the drawings in which:

FIG. 2 is a plan view of the invention as in FIG. 1, showing parts thereof broken away for clarity;

FIG. 3 is an elevational view of the patient support elements of FIG. 2;

FIG. 4 is a cross-sectional view of a portion of the head and torso element shown in FIG. 2;

FIG. 5 is a cross-sectional view taken along lines 5—5 of FIG. 2;

FIG. 6 is a perspective diagrammatic view of certain features of the underside of the torso section of the patient support surface of the invention;

FIG. 7 is a view similar to FIG. 4 but having a foamed core as an alternative embodiment;

FIG. 8 is a diagrammatic plan view of the x-ray cassette locking cams; and

FIG. 9 is a cross-sectional view similar to FIG. 4 illustrating an alternative embodiment of the invention.

Figure 1:
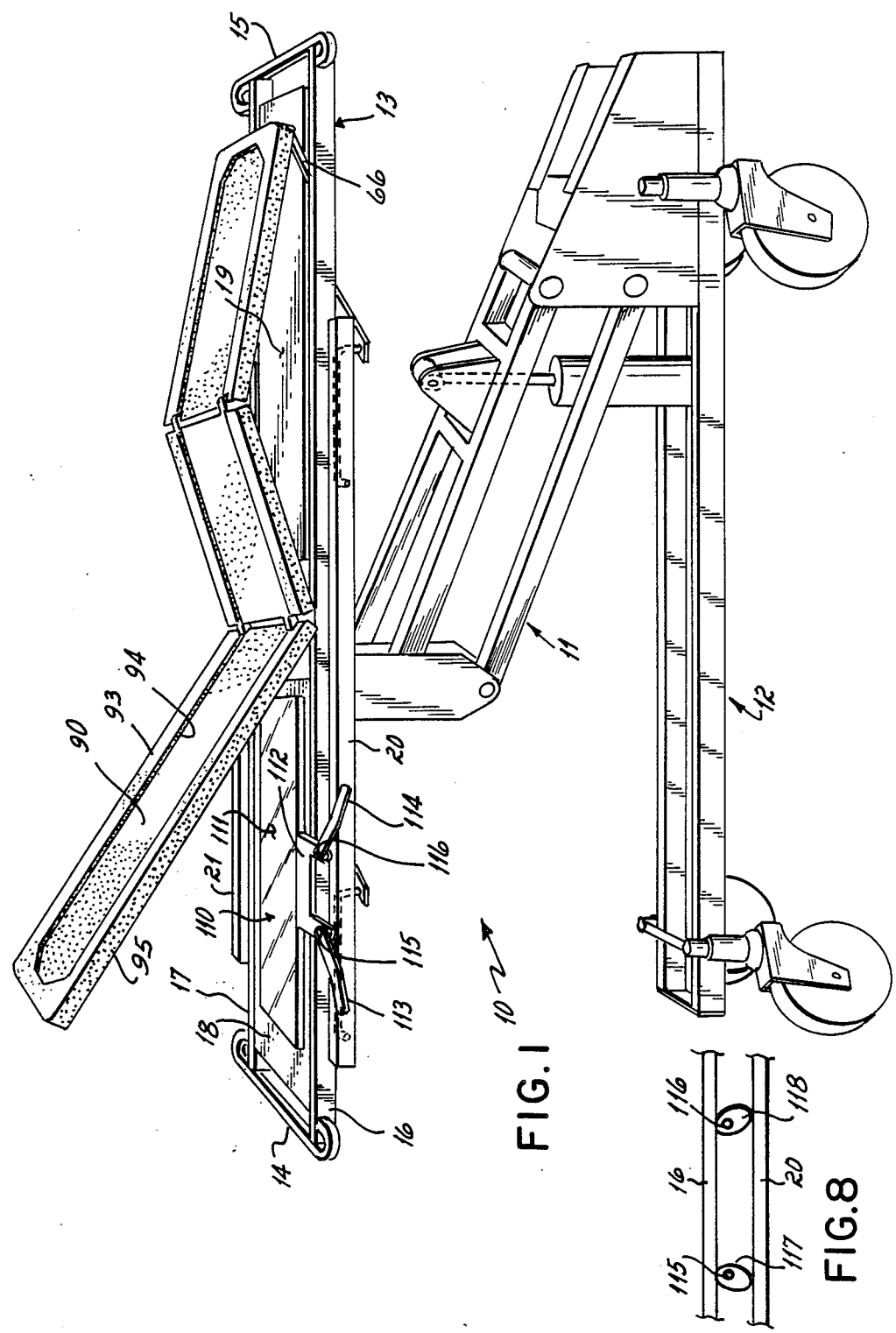
FIG. 1 is a perspective view illustrating a preferred embodiment of the invention as a hospital stretcher.

Turning now to the drawings there is shown in FIG. 1 a hospital stretcher 10 according to a preferred embodiment of the invention. While the embodiment of the invention shown in FIG. 1 has particular application and utility as a mobile hospital stretcher, it will be appreciated that the invention has other applications such as for hospital beds or other types of supports for patients. The apparatus 10 as shown in FIG. 1 is outfitted with wheels so that it can be moved about from place to place It includes a cantilevering lift apparatus 11, extending between the lower frame 12 and the upper supporting frame 13 and the apparatus it supports as will be described. The lift apparatus is similar to that which is disclosed in the commonly owned copending U.S. Pat. Application Ser. No. 7-034,232, filed on Apr. 2, 1987, specifically incorporated herein for reference.

It will be appreciated that the lift 11 and the lower frame 13 do not constitute any part of the particular invention of this present application. Suffice it to say that the lower frame 12 provides a stable mobile frame which can be moved about on the castors or wheels while the lift 11 provides a means for raising and lowering the support frame 13 as may be desired.

The support frame 13 includes end frame members 14 and 15, and two elongated side frame members 16 and 17. Side frame member 16 and 17 may also be joined together intermediate their ends by other frame members (not shown) Aluminum pans 18 and 19 extend across the side frame members 16 and 17.

The frame 13 is also provided with raisable side rails 20 and 21 which are shown in a lowered position in FIG. 1. In their lowered position, the side rails 20 and 21 lie in approximately the same plane as do the respective elongated side frames 16 and 17, and are spaced apart therefrom a predetermined distance as perhaps best seen in FIG. 2 and 8. When raised, the side rails inhibit a patient's inadvertent falling from the stretcher.

A patient support surface 25 is carried by support frame 13 and includes a head and torso support element 26, a hip and thigh support element 27, and a lower leg and foot support element 28. The elements 26, 27, and 28 are articulated about pivot axes 29 and 30 (FIG. 2) so that they can be positioned in a flat horizontal plane as indicated in FIG. 2 or in any articulated condition as shown in FIG. 1.

The pivot axis 29 is defined in part by trunnions 31 and 32 mounted on frame 13 and to which respective ends of the elements 26 and 27 are pivoted. Each of the elements 26 and 27 are provided with torque arms 33 and 34, respectively. Torque arm 33 is attached to a rectangularly-shaped frame 35 by means of brackets, such as the bracket 36 and frame element 37 as shown in FIG. 2. While bracket 36 and frame element 37 are only shown in the lower portion of FIG. 2, it will be appreciated that the upper portion has similar construction, which is simply not seen since it is beneath the patient support surface 25 in the upper part of FIG. 2. The rectangularly-shaped frame 35 includes side rails, such as at 38, and another parallel side rail on the opposite side of the element 26 (not shown in FIG. 2), as well as an end rail 39.

A bracket 40 is attached to the torque arm 33 and has one end attached to a pneumatic spring 41 which has an extensible rod 42 connected through a bracket 43 to a frame member 44. Any suitable and well-known pneumatic spring can be used. The spring 41 has an actuating button 45 located in the end of extensible rod 42. A lever 46 is secured to pivot bracket 47 which is mounted on the bracket 43, and is connected to actuating cables 48, which extend respectively to control handles 49 and 50 located at the left end of the apparatus as shown in FIG. 2. When at least one of the handles 49, 50 are squeezed outwardly, the cables 48 are tensioned, pulling the lever 46 toward the left hand or head end of the apparatus. In view of the fact that the lever 46 is pivoted at 51 to the bracket 47, the lever engages actuating button 45, releasing the pneumatic spring and permitting the piston 42 to extend. Extension of the piston 42 rotates the bracket 40 and the torque arm 33 in a clockwise direction with respect to the pivot axis 29, thereby raising the element 26 to a desired inclination. It will be appreciated that the cables 48 run through interior frame members, such as frame member 52, for example, secured to the outer side frame members 38 by means of bracket members 37 and 53, and providing further stiffening.

In a similar fashion, the torque arm 34 of element 27 is connected to the element 27 via brackets 55, frame members 56, inner frame members 57, and outer frame members 58. Additional frame elements 59 secure opposite ends of the inner and outer frames 57 and 58 together. Torque arm 34 is secured to one end of a bracket 60. The other end of the bracket 60 is connected to a pneumatic spring 61, actuated in similar fashion as that of spring 41 by means of cables 62, extending to control handles 63 and 64 at the right hand or foot end of the apparatus as viewed in FIG. 2. Operation of at least one of the control handles 63, 64 permits actuation of the pneumatic spring 61, causing torque arm 34 to rotate in a counter clockwise direction about pivot axis 29 and thereby raising the element 27 in a counter clockwise fashion to a position, for example, such as that shown in FIG. 1.

Upon this actuation, element 28 is carried by pivot elements 65 (FIG. 2) and a similar element not shown on the opposite side thereof, such that its end which is attached to element 27 is also raised. Each side of the opposite end of element 28 is provided with a pair of support links 66. Each link 66 has a lower end 67 operatively engaging a rack 68 on frame 13. As the element 28 is raised due to motion of the movable pivot axis 30, the end of the element 28 opposite the pivot axis 30 can also be raised and maintained in a desired position by means of the support links 66 and their interaction with the rack 68.

The head and torso support 26 of the patient support surface 25 is provided at its head end with legs 69 for supporting the patient support surface 25 slightly above the side rail 16 and 17 of the frame 13. A pair of legs 70, only one of which is shown in FIG. 3, is disposed on the patient support surface 25 beneath the axis 30 to support the elements 27 and 28 above the side rails 16, 17. Legs 71 are secured to the foot end of the element 28 and shown in FIG. 3 for supporting that end of the element above the side frames 16, 17, one leg 69, 70, 71 being located on each side of the patient support surface 25. Accordingly, it will be appreciated that the multiple element patient support surface 25 is articulated and is mounted on the frame 13 for positioning as described. Thus the patient's head and torso can be raised or a patient's thigh and lower leg area can be raised, and articulated at the patient's knees in order to provide an appropriate patient position.

Turning now to the patient support surface 25, it will be appreciated that surface is preferably comprised of three elements 26, 27, 28 as noted above. It will also be appreciated, however, that the support surface could be an integral support surface, not articulated, and lying in a common plane or in a plurality of planes as may be desired if movable articulation were not necessary. Also, it should be appreciated that the patient support surface 25 could comprise two, three, four or more elements articulated together as might be desired for any particular application.

The patient support surface 25, according to a preferred embodiment of the invention, provides a sufficiently rigid patient support surface so as to withstand the stress and strain of certain procedures, such as CPR, while at the same time providing a predetermined x-ray window which meets the one millimeter of aluminum equivalency standard of the F.D.A. and does not produce aberrations in the standard x-ray film which is normally utilized. Accordingly, it is contemplated that an x-ray plate can be placed beneath the patient support surface 25 for the purpose of receiving x-radiation directed through a patient supported on the surface 25 well within the F.D.A. standards.

In the drawings, it will be appreciated that the depiction of the patient support surface 25 in FIG. 1 is diagrammatic. Details of the patient support surface are more clearly shown in FIG. 2, wherein torso section 26 is provided with side hand holes 80, corner hand holes 81, and an end hand hole 82. The hip and thigh section 27 is provided with side hand holes 83. The foot section 28 is provided with side hand holes 84, corner hand holes 85 and end hand holes 86. The side and corner hand holes on the opposite side of the patient support surface 25 are not shown in FIG. 2 for clarity as those sections are broken away.

The structural details of the patient support surface are perhaps best seen in FIGS. 4, 5 and 6. FIGS. 4 and 5 depict particular sections of a typical patient support surface as represented by the head and torso section 26 of FIG. 2. It will be appreciated that the cross sections of the elements 27 and 28 of the patient support surface 25 are similar. Each of the elements 26, 27, and 28 are preferably constructed integrally by a blow molding process, such that each of the elements comprises a sheet-like patient supporting element 90, and an underlying, spaced apart, corrugated sheet-like reinforcing element 91. While blow molding is preferred, other processes such as injection molding or rotational molding could be used. As perhaps best seen in FIG. 5, the patient support element 90 is slightly spaced from the corrugated sheet-like reinforcing element 91.

Each of the elements 26, 27 and 28 has an integral blow-molded side structure (best seen in FIG. 5), which comprises an integral reinforced side frame 92. Integral side frame 92 includes a raised section 93 tapering down at 94 into the integral patient support element 90. The sidewalls of the element 26, as shown at 95 and 96 depend perpendicularly from the raised element 93 and are laterally spaced from an internal reinforcing rib defined by walls 97 and 98. It will be appreciated that the space between the facing walls 96 and 97 accommodate the interior and exterior frame members such as 52 and 38, respectively (FIG. 2) which themselves are preferably 1" by ¼" formed metallic tubing.

Accordingly, and from FIG. 5, it will be appreciated that the entire patient support surface 25 is integral, with the upper element 90 spaced from the lower element 91 such that the entire element, such as element 26 for example, can be blow molded. During the blow molding process, particular cores and the like are utilized in order to provide for the side, corner and end hand holes such as those illustrated at 80, 81 and 82 in FIG. 2, it being understood and appreciated that the various bends in not only the hand holes but in the edge walls 95, 96 and the reinforcing rib walls 97, 98 add to the rigidity of the entire patient support surface 25.

Again, it will be understood that while the cross section of FIGS. 4 and 5 are taken through the element 26, the element 27 and 28 preferably have similar cross sections.

Turning now momentarily to FIG. 4, it will be appreciated that the corrugated reinforcing element 91 has a series of elongated parallel ribs, including parallel crests or projections 99 and valleys or depressions 100 extending transversely across portions of the patient support surface 25 and the respective elements 26, 27 and 28. The crests 99 are slightly spaced from the patient supporting element 90, while the valleys 100 are further spaced from the patient support element 90. At the ends of the elements adjacent the pivots axis 29 and 30 for example, the patient supporting element 90 is curved to meet the reinforcing element 91 as at end 101 as shown in FIG. 4.

As shown in FIG. 5, each of the corrugations or ribs such as the rib 102, for example, terminates in a vertical wall 103, which is generally perpendicular to the patient supporting element 90. The vertical wall 103 provides significant support in a perpendicular direction with respect to the patient support element 90, and particularly upon any contact therewith.

It will be appreciated, particularly from FIG. 4, that the ribs, comprised of the alternating crests 99 and valleys 100 of the reinforcing element 91, are of uniform wall thickness. The walls of the ribs are disposed at an angle of no more than approximately 45° with respect to the patient supporting element 90. Accordingly, it will be appreciated that the combined thicknesses of the element 90 and 91 at any place through their cross section between the end walls 103, are substantially uniform, and will not produce undesirable aberrations or diagnostically significant artifacts on a standard x-ray plate.

For description purposes, FIG. 6 illustrates a predetermined area or radiolucent x-ray window "w" which is considered to be an x-ray window in the surface 25. This window lies over the surface 25 interiorly of end walls 103, the head and foot ends of the ribbed reinforcing element 91, and all frame structure.

While it is recognized that there is a very slight variation in the effective thickness of the element 91, depending on the precise location at which such thickness would be measured within the window "w", the thickness variation, caused by the angulation of the element 91 with respect to the element 90, is not sufficiently great enough to generate any aberration in an x-ray plate of the type normally utilized in a diagnostic x-ray procedure. It has been determined that if the angulation of the element 91 with respect to the patient support element 90 is maintained within this 45° range, vertical support walls beneath the patient and in the predetermined x-ray window are eliminated. Accordingly, there is no such support or reinforcing structure in the predetermined area "w". Aberrations or artifacts normally caused by such vertical walls in the area "w" are not produced on the standard x-ray plate placed beneath area "w". Thus electromagnetic waves directed through the predetermined area "w" are uniformly attenuated without aberrations so that an accurate x-ray picture can be formed.

Turning now to FIGS. 4 and 5, it will be appreciated that the patient support surface 25, and particularly its elements 26, 27 and 28, are preferably made of a synthetic material such as the plastic material known as NORYL 190, manufactured by The General Electric Company prior to this invention, use of this or of similar materials, in the thin sheets contemplated herein, was not suitable due to lack of rigidity which is required in the support. While NORYL 190 is a preferred material, other polymers and copolymers could be used. Preferably the wall thicknesses of elements 90 and 91 of the patient support surface 25 as illustrated by the arrows A and B of FIG. 4 are each preferably less than about 0.100" and particularly are preferably about 0.093", making the combined wall thickness approximately 0.186" throughout the predetermined area "w" as shown in FIG. 6. These wall surfaces are normally spaced apart at the peak 99 of the corrugated reinforcing element 91 a distance such that the overall thickness, including the distance "C" between the uppermost surface of the patient support element 90 to the lower surface of the reinforcing element 91 is approximately 0.250". Accordingly, the normal spacing between the reinforcing element 91 and the patient support element 90 at the crests 99 is approximately 0.064". In the preferred embodiment, the crests 99 are parallel and spaced apart about 4½" and the distance "D" is about 1". The entire support surface is about 26" wide. Element 26 is about 32½" long, element 27 about 24½" long and element 28 about 24½" long. The predetermined area "w" is about 18" wide between rib end walls 103 and about 26" long in a head-to-foot direction in element 26. The size of area "w" may be varied in the differing elements 26, 27 and 28 to accommodate a desired aberration-free x-ray window within the F.D.A. minimum equivalency standard.

When a patient is placed on the patient support surface 25 and on its various elements, it will be appreciated that the patient support element 90 may slightly deflect, coming into contact with the crest portions 99 of the underlying reinforcing element 91. Upon contact with the reinforcing element, further deflection of the patient supporting element 90 is significantly resisted such that the overall patient support surface 25 provides a rigid support for the patient. The surface 25 is thus capable of withstanding procedural stresses, such as any CPR stresses applied to the surface through the patient. The vertical wall sections 103 are close enough to aid in providing perpendicular resistance to deflections required, without impinging in the predetermined area "w". Also, the integrated structure of the support element, whether it is element 26, 27 or 28, serve to further rigidify each of the respective elements and resist deflection.

It should be kept in mind that while this preferred embodiment spaces the patient support element 90 from the crest portions 99, it is possible to select a molecular weight of polymer or copolymer and a process that would allow these portions to contact one another.

FIG. 9 shows one such type of contact wherein the reinforcing element 91a is integral with patient support element 90a at crest 99a in an alternative patient head and torso support element 26a. The thickness of the integral crest area 90a is preferably about the same as that of the patient support element 90a and reinforcing element 91a where not joined, in order to reduce or eliminate diagnostically significant artifacts.

In addition, it will be appreciated that an alternative embodiment of the patient support surface 25 might include similarly constructed elements but one or more having a foam material F deployed in the internal section of the patient support between the patient supporting element 90 and the reinforcing element 91. This could further rigidify and strengthen each particular patient supporting surface. This is shown diagrammatically in FIG. 7, which is similar to FIG. 4 with the exception of the illustration of the foamed core F. Like numbers in FIG. 7 designate elements like those of the preferred embodiment. In such a construction, the wall thicknesses of the elements 90 and 91, together with the foam material F are selected in order to meet the F.D.A. attenuation standards and yet at the same time provide a rigid patient support. While this foam-filled structure can meet the attenuation standards, it does create somewhat more of an artifact problem than does the previously described preferred embodiment.

In another aspect of this invention, (FIGS. 1, 2 and 8) the stretcher 10 is provided with an x-ray cassette 110, comprising a tray 111, a bracket 112, and actuating handles 113, 114. The tray is particularly configured for holding a standard x-ray plate (not shown). Each of the handles 113, 114 are secured via pins 115, 116 through bracket 112 to respective underlying cams 117, 118. The cams are respectively configured so that when the handle 113 is turned in a counter clockwise direction, and handle 114 in a clockwise direction, the cams present an enlarging ramp between the side rail 16 of the stretcher 10 and the lowered raisable side rail 20 as shown in FIG. 2. A diagrammatic picture of this is shown in FIG. 8. Accordingly, the cams are wedged between the frame rail 16 and the side rail 20 to retain the cassette 110 in its proper position. When the handles are rotated in the opposite directions respectively, the cassette can be loosened for adjustment forwards or backwards to properly mount an x-ray plate beneath the predetermined area or x-ray window "w". Of course, such a cassette is located above the aluminum pan 18 or above the aluminum pan 19 when performing x-ray procedures in the thigh or leg area. As noted above, each of the elements 27 and 28 include a predetermined area or x-ray window "w" which provides rigid patient support and uniform attenuation within the F.D.A. standard and similar to area "w" of element 26.

It will thus be appreciated that the invention provides a patient support surface having predetermined areas which provide uniform radiolucency therethrough such that there are no aberrations or diagnostically significant artifacts depicted on the normal-type x-ray plate and F.D.A. attenuation standards are met. Also, despite its preferably thin wall thicknesses, the patient support surface is sufficiently rigid so as to be capable of withstanding stresses and strains such as those normally applied to a patient support surface such as by CPR procedure, for example. The rigid structure in the preferred embodiment of the invention substantially resists deflection of the type of the which will tend to flex the patient support surface and cause it to fatigue or crack during normal usage. In addition, the integrated blow molded patient support surface elements provide unitary surfaces without cracks, depressions and joints which are difficult to clean.

It will also be appreciated that while the described corrugation configuration of the reinforcing element is preferred, other non-planar reinforcing element configurations might also be used to produce rigidifying results, maintain the F.D.A. attenuation standards, and provide aberration-free x-rays.

Moreover, it should also be appreciated that the invention renders possible the use of thin plastic materials which are highly radiolucent and which otherwise could not be used as a result of the interplay between the F.D.A. attenuation standard and the need for stress resisting rigidity Thus the selection of thin plastic materials which could not ordinarily be expected to be used for a radiolucent patient surface is made possible as a result of the invention.

These and other advantages and modifications will become readily apparent to those of ordinary skill in the art without departing from the scope of this invention, and the applicant intends to be bound only by the claims appended hereto.

I claim:

1. A patient surface comprising:
   a patient supporting member having a predetermined radiolucent area thereacross, and
   a non-planar radiolucent reinforcing member having portions disposed in operative, normally spaced-apart underlying relationship with said predetermined radiolucent area;
   wherein said patient supporting member and said reinforcing member are formed as one integral unit;
   said reinforcing member portions providing deflection resisting support for said patient supporting member when it is loaded.

2. A patient surface as in claim 1 wherein said patient supporting member in said radiolucent area and said reinforcing member thereunder in operative combination uniformly attenuate electromagnetic waves passing therethrough.

3. A patient surface as in claim 2 wherein said reinforcing member portions comprise a plurality of transversely extending projections defining crests and depressions underlying said radiolucent area of said patient supporting member.

4. A patient surface as in claim 3 wherein said crests are spaced from said patient supporting member when it is not loaded, and wherein said depressions are further spaced from said patient supporting member.

5. A patient surface as in claim 3 wherein said patient supporting surface and said reinforcing member are joined along respective edges thereof in a rigidifying elongated edge configuration perpendicular to said crests and depressions.

6. A patient surface as in claim 3 wherein said crests and depressions are defined by a corrugated sheet-like reinforcing element.

7. A patient surface as in claim 6 wherein the combined perpendicular wall thickness of said patient supporting member in said radiolucent area and of said underlying reinforcing member thereunder is substantially uniform and provides uniform radiolucency through said radiolucent area.

8. A patient surface as in claim 2 wherein said underlying reinforcing member is comprised of corrugated walls angulated throughout at less than 45° with respect to the plane of said patient supporting member.

9. A patient surface as in claim 2 wherein said reinforcing member comprises a plurality of rib forming walls disposed at angles other than perpendicularly to said patient supporting surface in order to provide uniform radiolucency therethrough.

10. A patient surface as in claim 3 wherein said patient surface includes at least two such integral units pivotally joined together.

11. A patient surface as in claim 1 including a core of foam material disposed between said patient supporting member and said reinforcing member.

12. A patient surface as in claim 3 wherein said patient supporting member and said reinforcing member are not normally spaced apart and wherein said crests are normally in contact with said patient supporting member.

13. A patient surface as in claim 12 wherein said crests and said patient supporting member are integral with each other.

14. A patient surface comprising:
a patient supporting member having a predetermined radiolucent area therein, and
a corrugated radiolucent reinforcing member having a plurality of ribs transversely disposed in operative, normally spaced apart and underlying relationship with said patient supporting member across said predetermined radiolucent area thereof when said patient supporting member is unloaded.

15. A patient surface as in claim 14 wherein said supporting member in said area and said underlying reinforcing member in combination uniformly attenuate electromagnetic waves passing through predetermined overlying areas thereof.

16. A patient surface as in claim 14 wherein the effective perpendicular combined thickness of said patient supporting member in said area and said underlying reinforcing member is substantially uniform.

17. A patient surface as in claim 14 wherein said ribs terminate in walls perpendicularly underlying said patient supporting member in a region outside said predetermined radiolucent area thereof.

18. A patient supporting apparatus comprising:
a stretcher frame having elongated side members and transverse members lying said elongated side members;
a trunnion mounted on each of said side members defining a pivot axis thereacross;
a patient support frame pivoted to said trunnion;
a patient support element mounted on said patient support frame and including:
a patient supporting member with a predetermined radiolucent area therein, and
a corrugated radiolucent reinforcing member having a plurality of ribs disposed in operative, normally spaced apart and underlying relationship with said patient supporting member across said predetermined radiolucent area thereof when said patient supporting member is unloaded.

19. A patient supporting apparatus as in claim 18 further including a second patient support frame pivoted to said trunnions and a second radiolucent patient support element mounted on said second patient support frame.

20. A patient supporting apparatus as in claim 19 further including a third patient support frame pivoted to said second patient support frame, and a third radiolucent patient support element mounted on said third frame.

21. A patient supporting apparatus as in claim 18, 19, or 20 wherein said ribs extend across said predetermined area and provide, in combination with said patient supporting member, uniform electromagnetic wave attenuation through said area.

22. A patient support element comprising:
a flat plastic sheet having a predetermined radiolucent area therein;
a corrugated plastic sheet underlying said flat plastic sheet, no section of said corrugated sheet underlying said predetermined radiolucent area forming an angle greater than 45° with respect to said flat plastic sheet;
and a perimeter structure outside said predetermined radiolucent area joining the peripheral edges of said sheets.

23. A patient support element as in claim 22 in which said sheets and perimeter structure are an integral structure 24. A support element as in claim 22 in which said corrugated sheet is out of contact with said flat sheet when support element is unstressed.

25. A patient support element as in claim 22 in which said perimeter structure includes parallel side structures that have ribs generally perpendicular to said flat sheet, the side structure providing resistance to bending of said patient support element.

26. A patient surface comprising:
a patient supporting member having a predetermined radiolucent area therein, and
a corrugated radiolucent reinforcing member having a plurality of ribs transversely disposed in operative, underlying relationship with said patient supporting member across said predetermined radiolucent area thereof,
the radiolucent area of said patient supporting member and the corrugated radiolucent reinforcing member thereunder comprising, in combination, a relatively uniform thickness for uniformly attenuating electromagnetic waves passing through both said radiolucent area, and said reinforcing member.

27. A patient surface comprising:
a patient supporting member having a predetermined radiolucent area thereacross;
a non-planar radiolucent reinforcing member having portions disposed in operative, normally spaced-apart underlying relationship with said predetermined radiolucent area;
said reinforcing member portions providing deflection resisting support for said patient supporting member when it is loaded;
wherein said patient supporting member in said radiolucent area and said reinforcing member thereunder in operative combination uniformly attenuate electromagnetic waves passing therethrough; and
wherein said reinforcing member portions comprise a plurality of transversely extending projections defining crests and depressions underlying said radiolucent area of said patient supporting member.

28. A patient surface as in claim 27 wherein said crests are spaced from said patient supporting member when it is not loaded, and wherein said depressions are further spaced from said patient supporting member.

29. A radiolucent patient surface as in claim 27 wherein said patient supporting surface and said reinforcing members are formed as one integral element, and are joined along respective edges thereof in a rigidifying elongated edge configuration perpendicular to said crests and depressions.

30. A radiolucent patient surface as in claim 27 wherein said crests and depressions are defined by a corrugated sheet-like reinforcing element.

31. A patient surface as in claim 30 wherein the combined perpendicular wall thickness of said patient supporting member in said radiolucent area and of said underlying reinforcing member thereunder is substantially uniform and provides uniform radiolucency through said radiolucent area.

32. A radiolucent patient surface as in claim 27 wherein said underlying reinforcing member is comprised of corrugated walls angulated throughout at less than 45° with respect to the plane of said patient supporting member.

33. A radiolucent patient surface as in claim 27 wherein said reinforcing member comprises a plurality of rib forming walls disposed at angles other than perpendicularly to said patient supporting surface in order to provide uniform radiolucency therethrough.

34. A radiolucent patient surface as in claim 27 wherein said patient supporting member and said reinforcing member are formed as one integral element, and wherein said patient supporting apparatus includes at least two such elements pivotally joined together.

35. A radiolucent patient surface as in claim 27 wherein said patient supporting member and said reinforcing member are not normally spaced apart and wherein said crests are normally in contact with said patient supporting member.

36. A radiolucent patient surface as in claim 35 wherein said crests and said patient supporting member are integral with each other.

* * * * *